(12) United States Patent
Babitshenko et al.

(10) Patent No.: US 11,650,205 B2
(45) Date of Patent: May 16, 2023

(54) SELECTIVE OPTICAL DETECTION OF ORGANIC ANALYTES IN LIQUIDS

(71) Applicant: QanikDX OÜ, Tallinn (EE)

(72) Inventors: Sergei Babitshenko, Tallinn (EE); Jaak Järv, Tallinn (EE); Aleksei Kuznetsov, Tallinn (EE); Anton Mastitski, Tallinn (EE)

(73) Assignee: QANIKDX OÜ, Tallinn (EE)

( * ) Notice: Subject to any disclaimer, the term of this patent is extended or adjusted under 35 U.S.C. 154(b) by 0 days.

(21) Appl. No.: 17/251,536

(22) PCT Filed: Jan. 20, 2020

(86) PCT No.: PCT/EP2020/051268
§ 371 (c)(1),
(2) Date: Dec. 11, 2020

(87) PCT Pub. No.: WO2020/164863
PCT Pub. Date: Aug. 20, 2020

(65) Prior Publication Data
US 2021/0356463 A1      Nov. 18, 2021

(30) Foreign Application Priority Data
Feb. 11, 2019    (EE) .................... U201900011

(51) Int. Cl.
*G01N 33/543*     (2006.01)
*G01N 33/542*     (2006.01)
*G01N 33/58*      (2006.01)
*G01N 21/64*      (2006.01)

(52) U.S. Cl.
CPC ... *G01N 33/54373* (2013.01); *G01N 21/6428* (2013.01); *G01N 33/582* (2013.01); *G01N 33/588* (2013.01); *G01N 2021/6441* (2013.01)

(58) Field of Classification Search
CPC ....... G01N 21/6428; G01N 2021/6441; G01N 33/5306
See application file for complete search history.

(56) References Cited

U.S. PATENT DOCUMENTS

2006/0134792 A1 * 6/2006 Kim ................... C12Q 1/706
                                                        436/6
2008/0064113 A1   3/2008 Goix et al.
(Continued)

FOREIGN PATENT DOCUMENTS

KR    100883547 B1    9/2008
KR    100970584 B1    9/2009
(Continued)

OTHER PUBLICATIONS

Alsager et al. (2014) "Small molecule detection in solution via the size contraction response of aptamer functionalized nanoparticles", Biosensors and Bioelectronics, vol. 57: 262-268.
(Continued)

*Primary Examiner* — Shafiqul Hao
*Assistant Examiner* — Nam P Nguyen
(74) *Attorney, Agent, or Firm* — Knobbe, Martens, Olsen & Bear, LLP

(57) ABSTRACT

A method and a device for detection and quantification of various organic analytes in a liquid sample and an assay substrate for providing analyte measurements. The method is implemented by using specific interaction of organic analytes with selective binding sites immobilized on a multi-layer assay substrate with further detection of such interaction with a device based on inducing and recording the fluorescence of the substrate for bio-chemical, genetic and environmental analyses.

16 Claims, 10 Drawing Sheets

(56) References Cited

U.S. PATENT DOCUMENTS

| | | | |
|---|---|---|---|
| 2008/0293164 | A1 | 11/2008 | Gaylord et al. |
| 2009/0186342 | A1 | 7/2009 | Bruno et al. |
| 2009/0227043 | A1 | 9/2009 | Huang |
| 2010/0285503 | A1 | 11/2010 | Bradshaw et al. |
| 2012/0040900 | A1 | 2/2012 | Alvarez et al. |
| 2012/0225491 | A1 | 9/2012 | Ram et al. |
| 2014/0349873 | A1 | 11/2014 | Bruno et al. |
| 2015/0323542 | A1 | 11/2015 | Barrett et al. |
| 2017/0341077 | A1 | 11/2017 | Neethirajan et al. |
| 2017/0370916 | A1 | 12/2017 | Liao et al. |
| 2018/0188243 | A1 | 7/2018 | Liao et al. |

FOREIGN PATENT DOCUMENTS

| | | |
|---|---|---|
| KR | 20110135775 B1 | 12/2011 |
| WO | WO 02/090987 A2 | 11/2002 |
| WO | WO 2007/016665 A2 | 2/2007 |
| WO | WO 2008/046029 A2 | 4/2008 |
| WO | WO 2010/074083 A1 | 7/2010 |
| WO | WO 2011/154918 A2 | 12/2011 |
| WO | WO 2017/037408 A1 | 3/2017 |
| WO | WO 2017/157980 A1 | 9/2017 |

OTHER PUBLICATIONS

Buchberger (2011) "Current approaches to trace analysis of pharmaceuticals and personal care products in the environment", Journal of Chromatography A, vol. 1218(4): 603-618.

Couto et al. (2016) "Recent developments, characteristics and potential applications of screen-printed electrodes in pharmaceutical and biological analysis", Talanta, vol. 146: 801-814.

Farré et al. (2007) "Recently developed GC/MS and LC/MS methods for determining NSAIDs in water samples", Analytical and Bioanalytical Chemistry, vol. 387(4): 1203-1214.

Kodoyianni (2011) "Label-free analysis of biomolecular interactions using SPR imaging", BioTechniques, vol. 50(1): 32-40.

Lara et al. (2016) "Applications of capillary electrophoresis with chemiluminescence detection in clinical, environmental and food analysis. A review", Analytica Chimica Acta, vol. 913: 22-40.

Long et al. (2013) "Recent advances in optical biosensors for environmental monitoring and early warning", Sensors vol. 13(10): 13928-13948.

Nguyen et al. (2007) "Biosensor-surface plasmon resonance: quantitative analysis of small molecule-nucleic acid interactions", Methods, vol. 42(2): 150-161.

Petrovic et al. (2010) "Recent trends in the liquid chromatography-mass spectrometry analysis of organic contaminants in environmental samples", Journal of Chromatography A, vol. 1217(25): 4004-4017.

Staples et al. (2001) "Ultimate biodegradation of alkylphenol ethoxylate surfactants and their biodegradation intermediates", Environmental Toxicology and Chemistry, vol. 20(11): 2450-2455.

Xu et al. (2010) "Review: Aptamers in microfluidic chips", Analytica Chimica Acta, vol. 683(1): 12-20.

Zhou et al. (2008) "A compact functional quantum Dot-DNA conjugate: preparation, hybridization, and specific label-free DNA detection", Langmuir, vol. 24(5): 1659-1664.

* cited by examiner a) b) c)

a)                                              b)

SELECTIVE OPTICAL DETECTION OF ORGANIC ANALYTES IN LIQUIDS

CROSS REFERENCE TO RELATED APPLICATIONS

This application is the U.S. National Phase of International Application No. PCT/EP2020/051268, filed Jan. 20, 2020, designating the U.S. and published in English as WO 2020/164863 A1 on Aug. 20, 2020. Any and all applications for which a foreign or domestic priority claim is identified here or in the Application Data Sheet as filed with the present application are hereby incorporated by reference under 37 CFR 1.57.

TECHNICAL FIELD

The invention relates to a method, system and/or device for detection of an organic analyte in a liquid, and more specifically to a method system and/or device for detection of an organic analyte in a liquid by using fluorescence to detect an interaction with a corresponding immobilized binding site.

BACKGROUND ART

Determination of small organic molecules in various natural liquid media is one of the most important and demanding tasks of bio-chemical, genetic, and environmental analyses, and different classical analytical methods are used to address these applications.

Express spectrometric -methods are widely used in environmental monitoring of water pollution, in scientific research and medical diagnostics. Various types of equipment have been developed, including portable devices for field analysis (Long et al. 2013). In these devices, in case of fluorescence spectroscopy, the known volume of sample is processed and placed in a test tube and fluorescence of this sample is measured at specific excitation wavelength. This is a simple and fast method of analysis, if the sample is characterized by sufficiently different excitation and emission spectral bands. Some complications can be connected with the need to calibrate the device for each type of sample to take into consideration the influence of additional emitters or quenchers of fluorescence signal, as well as the influence of opalescence caused by solid particles present in analysed samples. These factors complicate the analytical procedure and may cause the measurement error.

Such complications can be avoided if analyte is isolated from the liquid sample by the method of capillary electrophoresis and thereafter is detected with appropriate detector system by measuring, for example, UV spectrum or by using some another analytical method. This approach provides high detection sensitivity with application of portable devices (Lara et al. 2016). On the other hand, this method needs exact determination of the electrophoretic mobility of the analyte in different types of samples, as this parameter can be dependent on sample type. Moreover, properties of the capillary used for electrophoresis may also depend on sample properties and its variation in time. Therefore replacement of capillary and re-calibration of the device is necessary to do on regular basis. Finally, this method needs additional check that the output signal is caused only by the analyte and does not include signal generated by other components of similar mobility. Validation of these results can be done by using other analytical methods, which are free from these complications.

Among these methods the tandem technologies GC/MS, HPLC/MS or LCMS/MS (Buchberger 2010; Farre et al. 2007; Petrovic et al. 2010) have central position. Although different usable devices have been developed, these methods cannot be used without sample preparation and require trained staff. Most importantly, these devices have remained expensive, especially if real-time analytical runs are considered (Staples et al. 2001).

Electrochemical sensors are widely used in portable devices, which measure electric conductivity of the sample during some specific reaction taking place in the presence of analyte. These measurements can be made with great accuracy and the size of devices may be significantly reduced due to the possibility to use miniature chips with printed electrodes (Couto et al. 2015). The disadvantage of these sensors is connected with the detection procedure, where formation or disappearance of ionic compounds is measured in some set of consecutive reactions that occur in the presence of analyte, as each step of this reaction cascade may be influenced by the presence of impurities, properties of the reaction medium or temperature. All these factors contribute into uncertainty of the measurement, especially in the field conditions, and therefore these devices are mostly used for purposes of qualitative analysis.

More recently synthetic oligonucleotides, named aptamers, were proposed for binding analyte molecules. Aptamers form spatial molecular structure that specifically recognizes the whole analyte molecule or some part of its structure. Although discovery of aptamers has significantly widened analytical possibilities, based on creation of analytical chips with coatings sensitive to a particular analyte, still the absence of efficient and reliable detection methods has hindered development of cheap and efficient analytical and diagnostic devices.

Aptamers are widely used in combination with Surface Plasmon Resonance (SPR) technique (Kodoyianni 2011). In this case aptamers are immobilized on the chip surface and the complex formation process is recorded by monitoring the change of the molecular mass of this complex. Although this approach seems to be rather general, there are several significant disadvantages. Firstly, sensitivity of the senor depends on the presence of other compounds with similar binding groups in the sample. Secondly, it depends on the molecular mass of the analyte, and small molecules change the molecular mass of the complex not sufficiently for reliable detection (Nguyen et al. 2007). Therefore these measurements can be very problematic for analytes having low molecular mass. Additionally, these sensors may have high background signal due to non-specific binding of other components present in the sample. This high background signal reduces the sensitivity of this method. Finally, the process of complex formation can be too slow for fast and efficient measurements by using the SPR technique. These factors limit the application based on the aptamers.

Aptamers labeled with fluorescent dye were also introduced for determination of analytes in liquid media. According to this method, the analyte molecules are immobilized on the chip surface and thereafter dye-labeled aptamer is bound to these molecules. If additional analyte molecules appear in the solution, they compete with the immobilized molecules for the aptamer binding site and cause dissociation of the immobilized complex (Xu et al. 2010). As a result of this, the labeled aptamer molecules leave the surface of the chip and this changes fluorescence of the surface bound molecules (Alsager et al. 2014). The drawback of this method is the fact that the aptamer molecules remain in the assay medium even after their displacement, it is difficult to separate the fluorescence contribution of the surface-bound molecules and the displaced molecules.

Quantum dots in combination with the fluorescence resonance energy transfer (hereinafter referred as FRET, sometimes also called Förster resonance energy transfer) effect have been under consideration for use in many analytical applications, where the detection is performed in bulk sample volume, and quantum dots or their chemically modified analogs are dissolved or suspended in this volume. In this case, however, the signal depends strongly on the number of the emitting centers in the assay system, determined by the sample volume that should be measured with great precision (Zhou et al. 2008). This hampers the measurements and complicates calibration of the detection. Furthermore, the heterogeneity and transparency of the sample due to presence of solid particles or other reasons may hinder direct fluorescence measurements in the sample without its preliminary treatment and purification. This complicates wide application of fluorescence measurements in bulk sample volume.

Patent application US2009/0227043A1 (publ. Oct. 9, 2009) discloses a method, system and device for detection of an organic analyte in a liquid by using fluorescence to detect an interaction with a corresponding immobilized binding site. In said solution a transparent assay substrate is used having immobilized onto the surface of the substrate components for the detection of the organic analytes. In said solution the excitation/illumination is carried out through the surface of the assay substrate, that is from the other side of the assay substrate in order to minimize the optical interference caused by the components contained in the sample. The detection of the fluorescence is also carried out from below through the surface of the assay substrate. Said method, system and device has most of the disadvantages of the prior art described above.

Accordingly, there is a continuing need for an alternative method, system and/or device for detection of an organic analyte in a liquid that overcomes one or more of the disadvantages indicated above. It may be advantageous to provide a method, system and/or device that facilitates optical detection of organic analytes in a variety of different sample types without requiring isolation of the analyte from the sample.

DISCLOSURE OF INVENTION

The aim of present invention is to provide high selectivity and specificity for detection of various organic analytes in different liquids by using portable optical device, equipped with a set of assay substrates, which chemical composition is determined by the type of the analyte.

In other words, the aim of the present invention is to provide means (method, device) for determination of the absolute or relative abundance (often expressed as a concentration) of one, several or all particular organic analyte(s) present in a liquid sample.

To achieve the goals specified above the system for direct determination of analytes in a liquid sample of small volume is proposed. The system includes a detection method, an assay substrate and optical device for detecting analytes in aqueous solutions. The detection is based on the specific interaction of analyte molecule with the specific binding site of the sensor molecule bound with layered nanostructure immobilized on the surface of an assay substrate. The assay substrate is structured in a way to provide the FRET between quantum dots and fluorescence label of the analyte molecule bound with specific binding site on sensor molecule. Its surface is built as a layered structure, where different layers of chemical components are added to each on another, starting from the surface of the substrate. The assay substrate is analyzed with optical device providing excitation of fluorescence and recording the induced fluorescence flux due to FRET effect to derive the concentration of analyte.

The selectivity of the method is due to the interaction of analyte molecule with its specific binding site of sensor molecule, bound with layered nanostructure fixed on the surface of the assay substrate. This specific interaction causes the change of the fluorescence flux from said substrate, and such change is registered and used for the determination of analyte concentration. The distinctive feature of the method is the registration of the specific fluorescence from the interaction surface layer of the assay substrate without significant impact of the optical properties of the liquid sample and quenching of the emission by the sample matrix.

According to the first aspect of the invention there is provided a method for detection and quantification of at least one organic analyte in a liquid sample using specific interaction of said organic analyte with selective binding sites of sensor molecules based on the fluorescence resonance energy transfer effect (FRET).

Said detection and quantification is based on measurement(s) of such interaction based on the FRET effect.

Said method comprising:

providing an assay substrate configured with an assay substrate surface comprising a first component and a second component;

the first component comprising a sensor molecule labeled with a first fluorescent marker immobilized to the assay substrate surface with a first linker, the first linker being a bi-polar linker comprising a first binding group for specific binding of the first fluorescent marker and a second binding group for specific binding of the assay substrate surface, the sensor molecule having a specific binding site for the organic analyte, the sensor molecule labeled with the first fluorescent marker in a position that has no effect on the organic analyte binding the specific binding site;

the second component comprising a chemical analogue of the organic analyte, the chemical analogue labeled with a second fluorescent marker, the chemical analogue linked to the first fluorescent marker with a second linker having a length exceeding Förster radius, and the chemical analogue reversibly binding the specific binding site of the sensor molecule of the first component;

the first and the second components interacting to position the first fluorescent marker close to the second fluorescent marker at a distance shorter than the Förster radius to enable a FRET effect between the first and second fluorescent markers;

applying the liquid sample to the assay substrate;

illuminating the assay substrate with a light, spectrally fitting the excitation spectrum of the first fluorescent marker;

detecting fluorescence of the second fluorescent marker;

detecting the organic analyte by determining a decrease in fluorescence of the second fluorescent marker, due to the organic analyte displacing the chemical analogue from the specific binding site and subsiding the FRET effect.

In still yet another aspect there is provided, a device for detection of an organic analyte in a liquid sample, the device comprising:

an assay substrate configured with an assay substrate surface comprising a first component and a second component;

the first component comprising a sensor molecule labeled with a first fluorescent marker immobilized to the assay substrate surface with a first linker, the first linker being a bi-polar linker comprising a first binding group for specific binding of the first fluorescent marker and a second binding group for specific binding of the assay substrate surface, the sensor molecule having a specific binding site for the organic analyte, the sensor molecule labeled with the first fluorescent marker in a position that has no effect on the organic analyte binding the specific binding site;

the second component comprising a chemical analogue of the organic analyte, the chemical analogue labeled with a second fluorescent marker, the chemical analogue linked to the first fluorescent marker with a second linker having a length exceeding Förster radius, and the chemical analogue reversibly binding the specific binding site of the sensor molecule of the first component;

the assay substrate defining an assay substrate compartment for applying the liquid sample to the assay substrate surface;

a light source configured to emit a specific spectrum to induce the fluorescence of the first fluorescent marker;

an opto-electronic detector configured to detect fluorescence of the second fluorescent marker and generate a signal corresponding to fluorescence intensity;

a controller configured to record the signal from the opto-electronic detector and determine presence of the organic analyte based on a decrease of the detected fluorescence.

In some embodiments, the sensor molecule is selected from naturally occurring or synthesized molecules, including but not limited to proteins and oligonucleotides.

In some embodiments, the first fluorescent marker is a quantum dot (QD) with the fluorescence emission spectrum suitable for excitation of fluorescence of a second fluorescent marker.

In some embodiments, the said measurements are carried out in the thin layer of liquid sample, where the thickness of interaction surface layer of said liquid sample on the assay substrate is limited by (according to) physical restriction of Förster radius.

In some embodiments, said measurements of liquid sample is carried out without any preparation and/or pre-treatment of said sample used.

In some embodiments, the surface of substrate is solid and chemically inert.

In some embodiments, said substrate layers comprise at least one chemically linked first fluorescent marker with sensor molecule and an analyte analogue molecule to which the second fluorescent marker is bound.

In some embodiments, said first fluorescent marker is a quantum dot (QD) with the fluorescence emission spectrum suitable for excitation of fluorescence of a second fluorescent marker.

In some embodiments, said second fluorescent marker is a fluorescent dye with characteristic fluorescence emission spectrum distinguished from the fluorescence spectrum of a first fluorescent marker.

In some embodiments, said second fluorescent marker is a fluorescent protein with characteristic fluorescence emission spectrum distinguished from the fluorescence spectrum of a first fluorescent marker.

In some embodiments, the substrate comprises specifically defined analytical composition for single analyte measurements.

In some embodiments, the substrate comprises multiple analytical compositions for simultaneous measurements of multiple analytes.

In some embodiments, the substrate is made as a single use chip.

In some embodiments, said assay substrate is configured to receive for measurements no more than a microliter volume of sample.

In some embodiments, said optical scheme of the device is configured for fluorescence measurements from a single analytical composition on assay substrate.

In some embodiments, said optical scheme is configured for fluorescence measurements from multiple analytical compositions on assay substrate.

In some embodiments, said means of control and processing are configured to derive concentration of an analyte by relative decrease of recorded fluorescence in time from its initial value.

In some embodiments, the thickness of interaction surface layer of said liquid sample applied onto the assay substrate is limited according to physical restriction of Förster radius.

In some embodiments, the method further comprises quantifying an amount of the organic analyte in the liquid sample by measuring the decrease in fluorescence of the second fluorescent marker, the degree of the measured decrease corresponding to the amount of the organic analyte in the liquid sample.

In some embodiments, the second linker is sized to prevent binding of the chemical analogue with a specific binding site of a neighboring first component unlinked to the chemical analogue.

In some embodiments, the assay substrate is configured to bind a plurality of types of organic analytes, a plurality of types of sensor molecules respectively labeled with a plurality of types of first fluorescent markers immobilized on the same assay substrate surface, and the detected fluorescence having multi-spectral characteristics.

In some embodiments, the detecting of the organic analyte occurs in a thin layer of the liquid sample, the thickness of an interaction surface layer of the liquid sample on the assay substrate being limited according to the Förster radius.

According to the second aspect of the invention there is provided a method for detection and quantification of at least one organic analyte in a liquid sample using specific interaction of said organic analyte with selective binding sites of sensor molecules based on the fluorescence resonance energy transfer effect (FRET), where said method comprises steps, where:

in step 1 in initial stage said liquid sample containing organic analytes is applied to an assay substrate comprising at least one set of two interacting components constituting a sensor system:

said first component including a sensor molecule labeled with a first fluorescent marker and said marker is immobilized on the assay substrate surface via specific bi-polar linker;

where said sensor molecule has a specific binding site for an analyte under investigation;

where said sensor molecule is labeled with a first fluorescent marker in a binding position, where a connection of said chosen first labeling fluorescent marker has no effect on an analyte binding site;

where said bi-polar linker contains on one side specific binding group for a specific first fluorescent marker, and the opposite side contains the specific binding group for the processed substrate surface;

where the selection of a set of said linker molecules of various type provides simultaneous immobilization of a variety of first fluorescent markers bound with various sensor molecules on the same substrate surface;

said second component including chemical analogue of an analyte linked with a second fluorescent marker, where said chemical analogue of analyte is reversibly bound with said sensor molecule;

where said chemical analogue of analyte is linked with a first fluorescent marker with a linker having a length exceeding Förster radius (sometimes also referred as FRET radius);

where a set of said chemical analogues of various analytes is linked with specific sensor molecules having corresponding binding sites;

where said set of fluorescent markers has the distinguishing spectral characteristics; where the composition of the first and the second components are selected to bring a first fluorescent marker close to a second fluorescent marker such that the distance between said fluorescent markers is shorter than the Förster radius in order to enable FRET effect to occur between them, said composition corresponding to an initial stage of an assay substrate.

In step 2 in the initial stage immediately following the step of application of the organic analytes to an assay substrate said assay substrate is illuminated (excited) with a light, spectrally fitted with the excitation spectrum of a first fluorescent marker, and the energy transfer to a second fluorescent marker due to FRET effect takes place, inducing the fluorescence of a second marker, and said fluorescence is detected and its intensity is recorded, said detected fluorescence of the assay substrate at the initial stage corresponds to the spectral properties of a second fluorescent marker;

where said detected fluorescence has multi-spectral characteristics according to selected set of the sensor systems on the substrate surface.

In step 3 in the following stage over a predetermined period of time said excitation and detection is repeated at predetermined time intervals and each time the detected fluorescence intensity is recorded, allowing over said predetermined period of time at the presence of an analyte in a liquid sample introduced to the assay substrate, said analyte analogue molecules on the binding sites of sensor molecules to be substituted by the analyte molecules, and as result of such substitution said distance between two fluorescent markers to grow longer than the Förster radius, causing the subsiding of FRET effect in time.

In step 4 the amount of an analyte in a liquid sample is calculated/determined as decrease of fluorescence intensity of a second fluorescent marker recorded at said predetermined time intervals, where said decrease of fluorescence in time of second fluorescent marker is due to the subsiding FRET effect, and the degree of such decrease corresponds to the amount of an analyte in liquid sample.

In another aspect there is provided, an assay substrate for detection and quantification of various organic analytes in liquid sample, where said assay substrate is composed of layered nanostructures applied to the surface of the substrate.

In yet another aspect there is provided a device for providing an analyte measurements in a liquid sample comprising a light source, a sample compartment, an opto-electronic detector, controller, control unit and communication line, where said sample compartment for measurements is configured to receive an assay substrate carrying a micro volume of a liquid sample applied to said assay substrate;

the emission spectrum of said light source have been selected to induce the fluorescence of quantum dots on said assay compartment;

said opto-electronic detector is set up to detect the fluorescence of second fluorescent marker induced by energy transfer from quantum dot to said marker;

said electronic detector is set up to selectively detect the fluorescence of a set of various sensor systems immobilized on the assay substrate;

said control and processing means are set to record a time curve of said detected fluorescence of every sensor system in time to derive the concentration of an analytes;

said communication means are set to put out result of measurements.

In some embodiments, the controller of a device is configured to record the signal generated by the opto-electronic detector in time to determine the concentration of the organic analyte.

In some embodiments, the controller is configured to derive concentration of an analyte by relative decrease of recorded fluorescence in time from its initial value.

In some embodiments, the second linker is sized to prevent binding of the chemical analogue with a specific binding site of a neighboring first component unlinked to the chemical analogue.

In some embodiments, the assay substrate is configured to bind a plurality of types of organic analytes, a plurality of types of sensor molecules respectively labeled with a plurality of types of first fluorescent markers immobilized on the same assay substrate surface, and the controller configured to process a detected fluorescence having multi-spectral characteristics.

BRIEF DESCRIPTION OF DRAWINGS

Next, the present invention is described with the help of illustrations listed below, where.

BEST MODE FOR CARRYING OUT THE INVENTION

Figure 1:
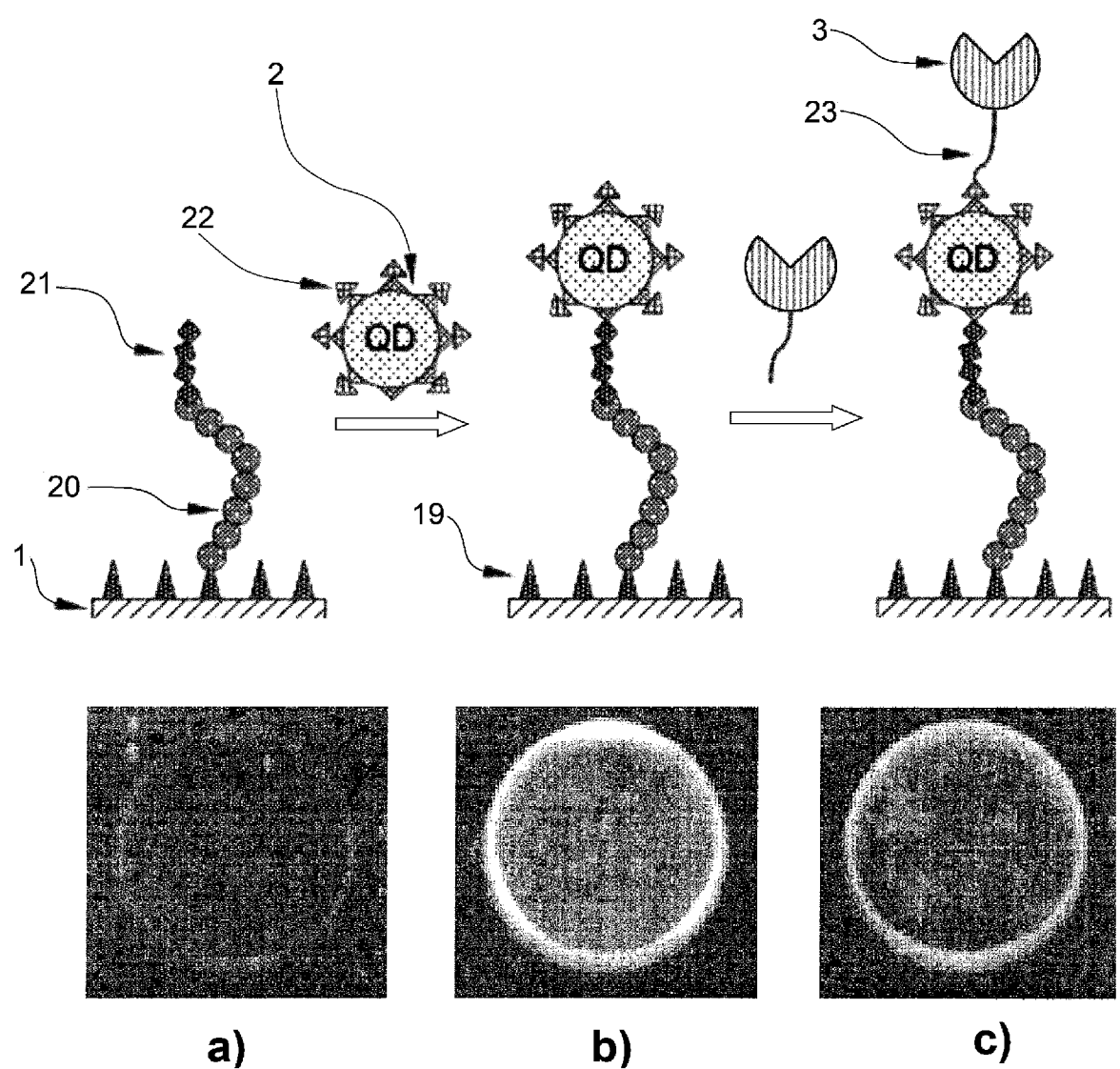
FIG. 1: Scheme and photos of reaction stages of substrate surface preparation: a)—structure of activated surface and form active centers; b)—structure of surface with immobilized QD (green color of the disk shows the presence of QD on surface); c)—structure of formation of immobilized complex of QD with analyte. 1—substrate surface; 2—quantum dot (QD); 3—sensor-like molecule; 19—reactive group on the substrate surface; 20—polymer linker; 21—bi-polar chemical linker; 22—reactive groups of QD for different linkers; 23—functional linker for binding the sensor molecule with QD.

A detection method, system and/or device, structure of the assay substrate and optical device for detecting analytes in aqueous solutions is described herein.

In proposed analytical assay the detection of the analyte is done by the FRET effect, caused by the energy transfer between quantum dots and fluorescent label of the analyte molecule bound with specific analyte binding site. The high selectivity of this method is achieved through the interaction of analyte molecule with the specific binding site of sensor molecule, bound with layered nanostructures on the surface of the assay substrate. Such substrate can be a plate, chip, sphere or any other spatial structure having solid surface with multi-layer arrangement on it aimed to interact with liquid sample. The composition of the assay substrate materials and its specific interaction with the analyte molecule define the optical signal from the assay substrate in the form of characteristic fluorescence emission. This emission is registered and used for the determination of analyte concentration.

The measuring system comprises substance-specific assay substrate and the device for inducing and detecting the specific fluorescence of it. The specificity of the system for targeted analyte type is determined by the multi-layer composition of the substrate, while the detection remains the same. Important feature of the system is the registration of fluorescence signal from fixed surface layer of interaction on the assay substrate without significant impact of the optical properties of the liquid sample and quenching of the emission by the sample matrix. To reach these conditions and to get fixed the thickness of the measured surface layer, the FRET with participation of quantum dots is used, as this effect is sensitive to the intermolecular distance and can be measured only within the range of the Förster radius (Lakowicz 2006).

The assay substrate of the measuring system includes the following two interacting components. The first component includes a sensor molecule labeled with a first fluorescent marker, and said marker is immobilized on the substrate surface via composite linker. Such sensor molecule has a specific binding site for an analyte under investigation, and therefore selectively binds an analyte molecule. The particular feature of proposed system is the possibility to use various sensor molecules with analyte specific binding sites. The embodiments of such sensor molecules may include proteins, oligonucleotides or synthetic molecules, which selectively interact with the analyte molecule. The sensor molecules are labeled with a first fluorescent marker, for example by a quantum dot (QD), in a position, where this labeling has no effect on analyte binding site. This is the first functional requirement for the assay substrate structure. And such first component is also bound with the second interacting component.

The second component includes chemical analogue of an analyte linked with a second fluorescent marker. The second marker can be a fluorescent organic dye or fluorescent protein bound by suitable linker with chemical analogue of the analyte, which should be able to interact with the binding site of the natural or synthetic sensor molecule.

It is essential that the spectrum of characteristic fluorescence emission of a first fluorescent marker is distinguished from the fluorescence spectrum of a second fluorescent marker and is suitable for the excitation of fluorescence of a second fluorescent marker.

The advantage of such system is in providing quantitative results of the analysis with liquid sample introduced to the assay substrate without sample preparation and preliminary processing, thus simplifying the analysis procedure. Another advantage is that the analysis is performed in a small volume of liquid sample, which is essential for use of the method in applications with limited sample volume. And additional enhancement provided by such system is the reliable detection of analyte not depending on the optical properties of the samples, equally applicable for transparent and opaque liquids, and for samples containing solid particles, on the surface of the assay substrate.

To reach these conditions and to get fixed thickness of the interacting surface layer, the FRET with participation of quantum dots is used. This effect takes place only within the range of the Förster radius (typical scale up to 10 nm), and the latter defines the thickness of measured layer on the assay substrate. Layered nanostructures, composed of a quantum dot fixed on an inert solid surface of the assay substrate with composite linker and chemically linked with sensor macromolecule with specific binding site for analyte, that is reversibly connected with analyte analogue molecule, to which dye label labeled is bound, provide the distance between a quantum dot and a dye label within the Förster radius.

The method of detection according to preferred embodiments works as following. The assay substrate in the initial stage provides the fluorescence flux according to FRET effect. When the studied liquid containing analyte molecules is added to the assay substrate, the analyte analogue molecule is displaced from the layered nanostructure by the analyte. Such displacement stops the FRET effect. The change of fluorescence flux is registered by the optical device and used for determination of the analyte concentration.

The functionally active assay substrate is formed by combination of two abovementioned components, and these two components form complex on the substrate surface. Such complex brings a first fluorescent marker close to a second fluorescent marker making the distance between said fluorescent markers shorter than the Förster radius to enable FRET effect between them in the characteristic spectral range. Such composition is referred as a sensor system at the initial stage of an assay substrate. This closeness of the QD and fluorescent dye is the second functional requirement when positioning of the analyte analogue molecule marked with dye molecule in the sensor molecule.

When the assay substrate in the initial stage with added liquid sample is illuminated (excited) with a light, spectrally fitting the excitation spectrum of a first fluorescent marker, and the energy transfer to a second fluorescent marker takes place due to FRET effect inducing the fluorescence of a second marker, and the observed fluorescence of the assay substrate corresponds to the spectral properties of a second fluorescent marker. This is referred as the starting point of the analysis.

If analyte molecules are present in the studied sample, these molecules compete with the reversibly bound analyte analogue molecules (the second component of the assay substrate) for selective binding sites on the sensor molecule (the first component of the assay substrate) and substitute in time an analyte analogue molecules on the binding sites of sensor molecules, thus the displacement of the analyte analogue molecules from the substrate surface occurs in time. Due to this the distance between two fluorescent markers, e.g. between the surface-bound QD and the analyte analogue bound fluorescent label, increases and exceeds the Förster radius, and that shuts off the FRET effect. Then the observed fluorescence of the assay substrate with liquid sample corresponds to decreasing in time fluorescence of a second fluorescent marker due to subsiding FRET effect. The degree of decrease of the FRET signal is determined by analyte concentration in the sample and this decrease is used to calculate the analyte concentration in the sample under examination. Because the concentration of an analyte is derived by relative decrease of recorded fluorescence in time from its initial value, the device does not require any adjustments.

Preferred embodiment provides a method for detection and quantification of at least one organic analyte in a liquid sample using its specific interaction with selective binding sites of sensor molecules with further measurement of such interaction based on the FRET effect. Said method comprises steps specified below.

In step 1 said liquid sample containing organic analytes is applied to an assay substrate comprising at least one set of two interacting components:

said first component including a sensor molecule labeled with a first fluorescent marker, and said marker is immobilized on the assay substrate surface with composite linker, where said sensor molecule has a specific binding site for an analyte under investigation;

where said sensor molecule is labeled with a first fluorescent marker in a binding position, where said chosen first labelling fluorescent marker having no effect on an analyte binding with its binding site;

said second component including chemical analogue of an analyte linked with a second fluorescent marker and bound with said first component;

where the composition of the first and the second components are selected to bring a first fluorescent marker close to a second fluorescent marker such that the distance between said fluorescent markers is shorter than the Förster radius in order to enable FRET effect to occur between them, said composition corresponding to an initial stage of an assay substrate.

In step 2 in the initial stage immediately following of the step of application of the organic analytes to an assay substrate said assay substrate is illuminated (excited) with a light, spectrally fitted with the excitation spectrum of a first fluorescent marker, and the energy transfer to a second fluorescent marker due to FRET effect inducing the fluorescence of a second marker is detected and fluorescence intensity is recorded, said detected fluorescence of the assay substrate at the initial stage corresponds to the spectral properties of a second fluorescent marker.

In step 3 in the following stage over a predetermined period of time said excitation and detection is repeated at predetermined time intervals and each time the detected fluorescence intensity is recorded, allowing over said predetermined period of time at the presence of an analyte in a liquid sample introduced to the assay substrate, said analyte analogue molecules on the binding sites of sensor molecules to be substituted by the analyte molecules. As result of such substitution said distance between two fluorescent markers increases longer than the Förster radius, causing the subsiding of FRET effect in time.

In step 4 the amount of an analyte in a liquid sample is calculated/determined as decrease of fluorescence intensity of a second fluorescent marker recorded at said predetermined time intervals, where said decrease of fluorescence in time of a second fluorescent marker is due to the subsiding FRET effect, and where the degree of such decrease corresponds to the amount of an analyte in liquid sample.

Preferably said sensor molecule is selected from naturally occurring or synthesized molecules, including but not limited to proteins and oligonucleotides.

Preferably said first fluorescent marker is a quantum dot (QD) with the fluorescence emission spectrum suitable for excitation of fluorescence of a second fluorescent marker.

Preferably said second fluorescent marker is a fluorescent dye with characteristic fluorescence emission spectrum distinguished from the fluorescence spectrum of a first fluorescent marker.

Preferably all measurements are carried out in the thin layer of liquid sample, where the thickness of interaction surface layer of said liquid sample on the assay substrate is limited according to (by) physical restriction of Förster radius.

Preferably said measurements of liquid sample are carried out without any preparation and/or pretreatment of said sample used.

According to preferred embodiment also an assay substrate is provided for detection and quantification of various organic analytes in liquid sample, said assay substrate is composed of layered nanostructures applied to a surface of the substrate.

Said surface of substrate is solid and chemically inert.

Said layers of layered nanostructures comprise at least one chemically linked first fluorescent marker with sensor molecule and an analyte analogue molecule to which the second fluorescent marker is bound.

Preferably, said first fluorescent marker is a quantum dot (QD) with the fluorescence emission spectrum suitable for excitation of fluorescence of a second fluorescent marker.

Preferably, said second fluorescent marker is a fluorescent dye with characteristic fluorescence emission spectrum distinguished from the fluorescence spectrum of a first fluorescent marker.

Preferably, said second fluorescent marker is a fluorescent protein with characteristic fluorescence emission spectrum distinguished from the fluorescence spectrum of a first fluorescent marker.

According to first preferred embodiment, said assay substrate comprises specifically defined analytical composition constituting a sensor system for single analyte measurements.

According to second preferred embodiment, said assay substrate comprises multiple analytical compositions for simultaneous measurements of multiple analytes.

According to third preferred embodiment, said assay substrate is made as a single use chip.

According to forth preferred embodiment, said assay substrate is configured to receive for measurements no more than a microliter volume of sample.

Preferred embodiment covers also a device for analyte measurements in a liquid sample.

The device for analyte detection includes besides the assay substrate also the following constituent parts:
 the light source with a light beam at preselected emission wavelength to induce the assay substrate fluorescence;
 the assay substrate compartment to introduce and measure the liquid sample;
 the opto-electronic detector to record the fluorescence caused by FRET effect;
 the means of control, processing and communication to manage the measurements, determine concentration of the analyte, and to report the result.

For carrying out the method according to the invention a device is provided for detection and quantification of at least one organic analyte in a liquid sample using specific interaction of said organic analyte with selective binding sites of sensor molecules based on the fluorescence resonance energy transfer effect.

Said device for providing analyte measurements in a liquid sample according to preferred embodiment comprising a light source, a sample compartment, an opto-electronic detector, controller, control unit and communication line.

Said sample compartment for measurements is configured to receive an assay substrate carrying a micro volume of a liquid sample applied to said assay substrate.

The emission spectrum of said light source has been selected to induce the fluorescence of quantum dots on said assay compartment.

Said opto-electronic detector is set up to detect the fluorescence of a fluorescent marker of a chemical analogue of the organic analyte induced by energy transfer from quantum dot to said marker.

Said control and processing means are set to record a time curve of said detected fluorescence in time to derive the concentration of an analyte.

Said communication line is set to put out result of measurements.

According to first preferred embodiment of the device, said optical scheme of said device provides fluorescence measurements from single composition on assay substrate.

According to second preferred embodiment of the device, said optical scheme of said device provides fluorescence measurements from multiple analytical compositions on assay substrate.

According to preferred embodiment of the device, controller provides operation control and signal processing to derive concentration of an analyte by relative decrease of recorded fluorescence in time from its initial value.

According to preferred embodiment of the device, the thickness of interaction surface layer of said liquid sample applied onto the assay substrate is limited according to (by) physical restriction of Förster radius.

Finally, the described method for determination of a target substance in a liquid sample has the following distinguishing properties:
 1. The selectivity and the sensitivity of the detection procedure are determined by specific binding site of the sensor molecule, and if the naturally occurring sensor molecules, namely proteins and oligonucleotides, are used in the assay substrate, it gains selectivity and sensitivity that corresponds to relevant (meaningful) analyte levels in appropriate samples.
 2. The detectable fluorescence signal, caused by FRET effect, has specific emission spectrum and can be easily separated from the fluorescence emission of QD and is completely quenched by displacement of the labeled analyte analogue molecule from its complex with sensor macromolecule.
 3. Strict localization of the FRET emission on the surface of the assay substrate reduces obstacles caused by optical properties of liquid sample, makes the detection independent on the sample volume, and eliminates the need of sample treatment.
 4. The measurement of relative fluorescence makes said device insensitive to non-specific adsorption of any contamination of an assay substrate.
 5. Only microliter volume of sample is needed for the analysis.
 6. The thickness of detection layer of liquid sample is physically restricted by Förster radius and does not depend on the optical properties of sample media.
 7. It is possible to get a single- or multiple analytes detection with the assay substrate by having a single or multiple analytical composition on it.
 8. The assay substrate interacts with a liquid sample, and therefore is of single use design.
 9. Analysis is done in one step without need for sample preparation and control of the properties of liquid sample.
 10. The detection is not sensitive to the impurities, suspended solids, viscosity, or sample opacity.
 11. The system does not require adjustments and calibrations with standard sample solutions.
 12. The detection is not sensitive to non-specific adsorption of any contaminants on the substrate surface.

The assay substrate is built as a layered structure, where different layers of chemical components are added to each on another, starting from the surface of the substrate (FIG. 1). The material of the surface should be easily processed to allow formation of the desired shape and thickness, should allow it's fixing to the substrate body, and should carry chemically active groups for covalent linking of the assay components. Such material can be a thin mica plate, which can be easily processed to thin plates with a smooth surface, is optically permeable in the near UV region, and its surface can be chemically modified. The layered structure of mica is important for the preparation of substrates with identical properties.

Quartz glass can also be applied for design of the assay substrate, it has also surface hydroxyl groups which can be used for chemical modification of this material, and its optical transparency is almost complete. As this material is mechanically fragile, sophisticated methods are needed for mechanical processing of this material that makes its usage expensive and complicated in comparison with mica.

The use of plastics is a universal solution for this application. These materials can be easily processed to obtain necessary shape with controlled thickness and their surface groups can serve as linkers for further chemical modification, and there is a wide range of plastics with different composition of the surface groups. Optical properties of plastics are strongly related with their chemical composition, as aromatic rings and large conjugated structures may strongly absorb UV radiation. But still there are several materials which can be used for design of the assay substrates for this application, like poly(methyl-methacrylate) (PMMA) and its derivatives.

After selection of the substrate material chemical processing of the surface should be made together with activation of the functional groups. As the surface of the selected material may be soiled and contaminated, cleaning process of this material should be applied by using efficient mechanical or electrical methods and/or washing with solvents.

For activation of surface groups of mica or quartz glass these materials are treated with 1 M hydrochloric acid during 1 hour at elevated temperature of about 50° C. After washing with bi-distilled water the material is dried during 12 hours at 110-120° C. to remove moisture from the pores of the material. Plastics, which are not resistant to high temperature, are dried in vacuum.

The activated and cleaned surface of substrate is processed with 20% solution of (3-aminopropyl) trimethoxysilane (APTMS) in 20% toluene during 12 hours at room temperature. This reaction time is enough to form a layer of highly reactive groups (19, FIG. 1) on the substrate surface, serving as reaction sites for linker attaching the next layer of the layered structure of the assay substrate.

The surface inhomogeneities may cause spotty distribution of reactive groups, and therefore influence the spatial characteristics of the next layer, potentially limiting the density and concentration of the senor systems on it. To eliminate such influence of the surface inhomogeneities to immobilization of the sensor systems, the substrate surface (1) is covered with polymer layer containing a polymer linker (20), e.g. PEG, characterized with high chemical stability and having reactive groups for binding the bi-polar linker (21) of the next layer. Chemical composition of the linker molecules (21) depends on the chemical nature of the next structural layer. However, in general, this bi-polar linker should have two reaction groups. One group of is needed for its covalent binding with the silanized surface of the substrate material through the polymer layer (20). The second group is needed for binding to functional groups (22) attached to quantum dots (2). To avoid side reactions the second linker group is protected and can be de-protected after reaction of the first linker group with the substrate surface.

The next structural layer consists of immobilized quantum dots (2). This immobilization reaction depends on nature of chemical groups (22) planted on the surface of quantum dots to minimize possibility of aggregation of these particles in a solution. Such functional groups serve to link quantum dots with various sensor molecules (8), and the chemical structure of these functional groups determine strategy of the synthesis of a sensor system.

In some cases, it could be possible to replace quantum dots with organic fluorophore or fluorescent proteins and still have comparable quantum yield of fluorescence. However, this replacement of quantum dots is accompanied by the following limitations. Firstly, it is not possible to create multivalent fluorophore, which is able to bind simultaneously several sensor molecules. The second complication is connected with partial overlapping of excitation and emission spectrums of organic fluorescent dyes or proteins. Therefore this fluorophore replacement may be connected with requirement for a very narrow excitation band and need for pulse-mode usage. These disadvantages are precluded by spectral properties of quantum dots.

As the following example describes application of quantum dots with carboxylic groups on their surface, immobilization of these particles on the substrate surface is made via amide bond. Therefore the second functional group of the linker molecule is amino group. As usual for amide formation reactions, the carboxyl groups are activated by adding EDC and NSH that helps to finish the coupling reaction during 1 hour at room temperature. The quantum dots used in an example are characterized by the fluorescence emission at 540 nm (green).

To create the next structural layer on the assay substrate, the quantum dots were further modified with the functional linker (23). As the carboxyl groups of quantum dots, remaining on the outer surface of the structural layer, were used for coupling with the second linker via amide bond formation, the first functional group of the functional linker is again amino group.

To reduce degradation of the immobilized quantum dots during reaction with the functional linker, this coupling was made in non-aqueous reaction medium, for example in DMFA. For this reaction the substrate containing immobilized quantum dots are treated with activator and thereafter reacted with the linker. This coupling reaction is complete during 30 min at room temperature and the excess of reagents can be removed by washing the substrates.

The second functional group of the functional linker depends, however, on structure of the functional group of the sensor molecule (8) of the assay substrate. This sensor molecule is bound to the outer layer of the layered structure of the substrate, and it changes the spectrum of the substrate due to its specific interaction with the analyte. This change is monitored by the device and is used for calculation of the analyte concentration on the assay substrate. As different analytes need different sensor molecule, the functional linker used for coupling of these molecules should allow wide variation of structure of the second functional group.

Although different sensor molecules can be used for this assay substrate, including polymeric structures or biopolymers, all these sensor molecules should have several common characteristics: they should specifically interact with the analyte, and this interaction should change fluorescence spectrum of the assay substrate.

Schematic illustration of all steps of preparation of the assay substrate is shown in FIG. 1 together with photos of the resulting substrate irradiated with UV light at the wavelength of 312 nm. The initial substrate material on photo (a) is fully transparent and does not provide any light emission at UV excitation, while visible fluorescence (of green color) due to immobilized QD on the substrate in the photos (b) and (c) confirms that the multi-layer structure obtained by the described procedure has the required spectral and chemical characteristics.

Figure 2:
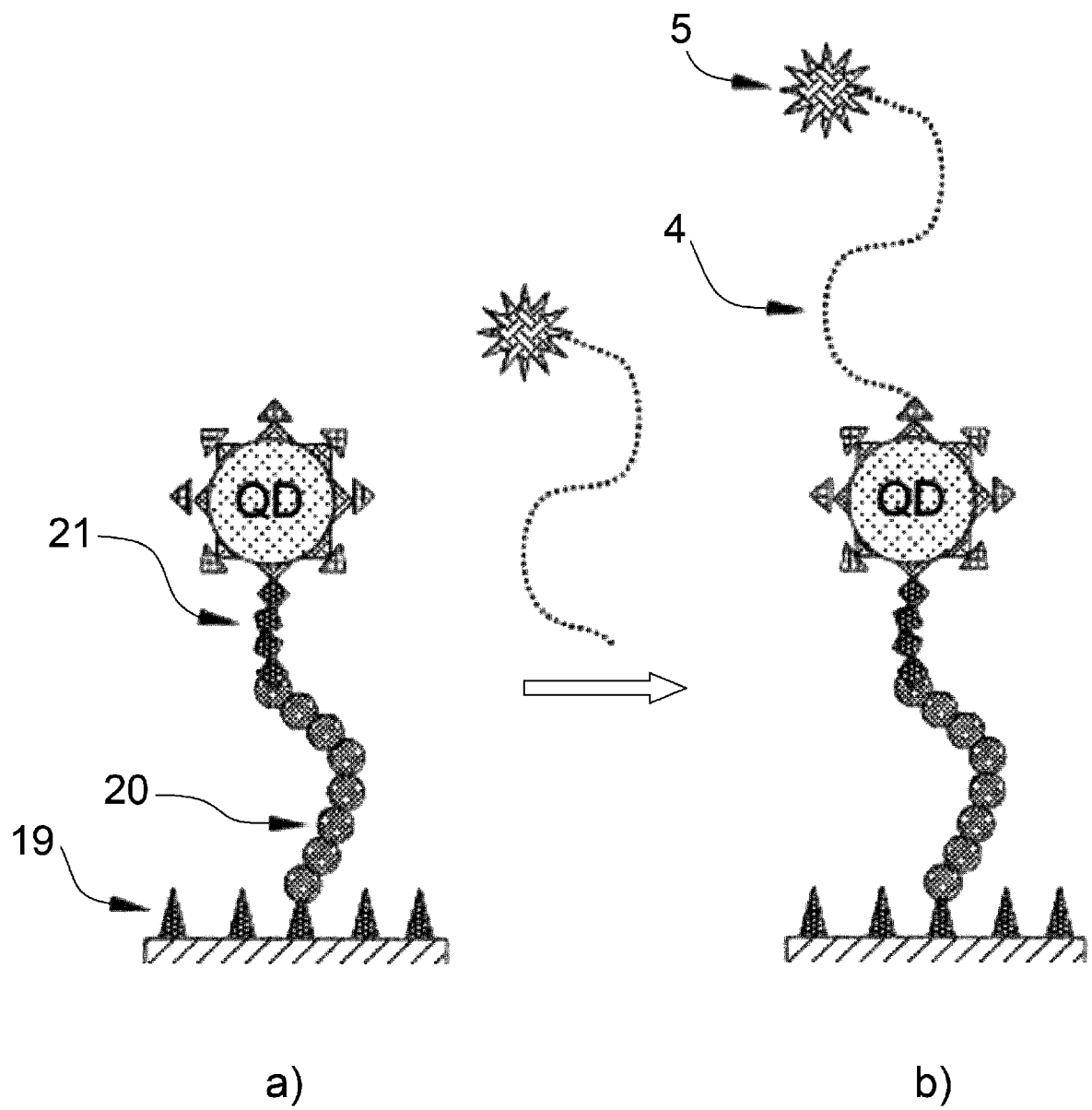
FIG. 2: The scheme of fluorescence of assay substrate: (a) substrate surface with immobilized QD (non-FRET system); (b) assay substrate with FRET system: 4—linker for fluorescent dye; 5—fluorescent dye; 19—reactive group on the substrate surface; 20—polymer linker; 21—bi-polar chemical linker.

For characterization of the FRET effect on the same assay substrate the model system is constructed as is illustrated in FIG. 2, where the fluorescent dye 5(6)-carboxytetramethylrhodamine (TAMRA) (5) is linked with oligopeptide and thereafter is coupled with the immobilized quantum dots with linker (4). As the excitation wavelengths of this dye are the same as emission wavelength of the used quantum dots (530-540 nm), FRET effect can be observed in this model system.

Figure 3:
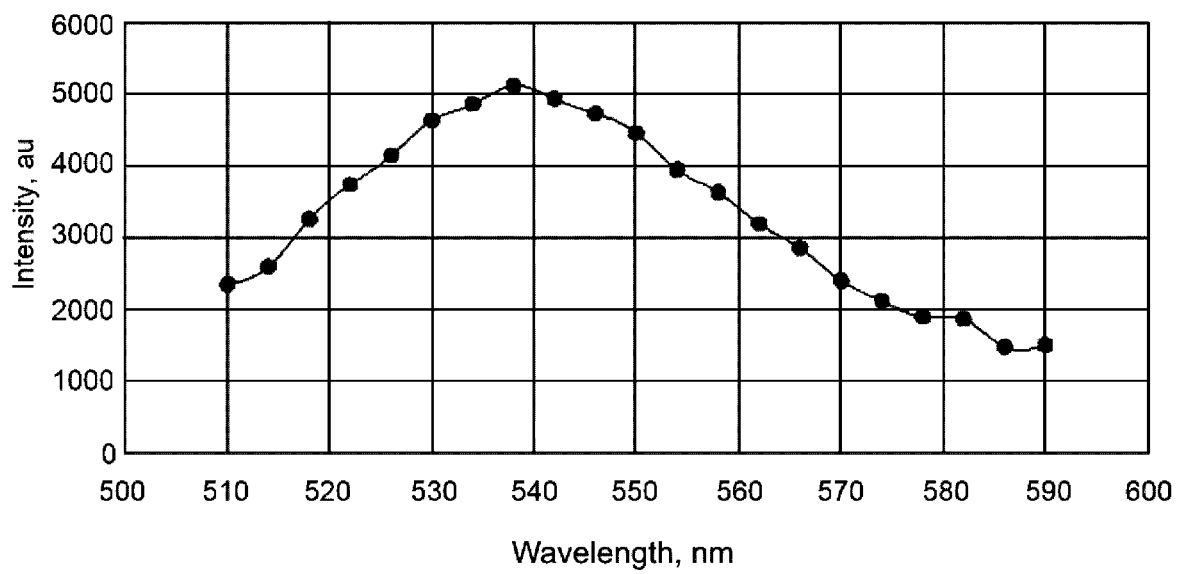
FIG. 3: Emission spectrum of model substrate without (a) and with a dye-labeled agent (b) at the excitation wavelength of 320 nm.
Figure 3:
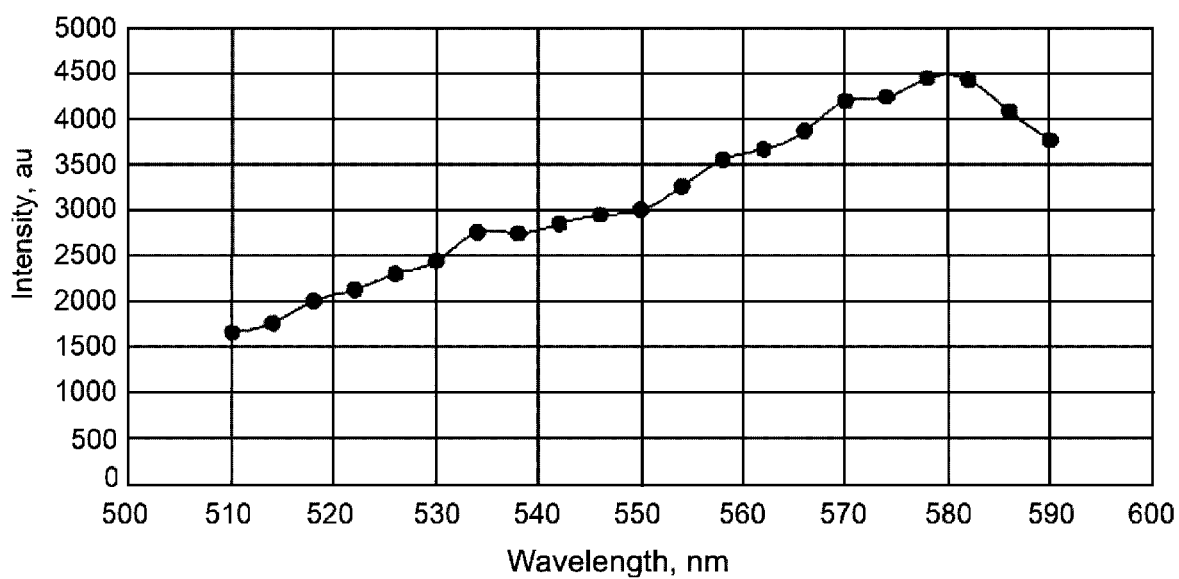

In FIG. 3 fluorescence spectra for assay substrate according to FIG. 2 with immobilized TAMRA and without this dye are compared. It is clearly seen that the substrate with immobilized quantum dots emits visible green color (maximal spectral intensity at 540 nm), while the substrate carrying also the immobilized dye molecule is colored orange, which corresponds to the emission wavelength 580 nm for TAMRA.

This change in the fluorescence spectrum is characterized in detail by means of the device described in the preferred embodiment. The excitation at 360 nm was used in both cases. In the case of substrates with immobilized quantum dots the emission peak is observed at 540 nm, and at wavelength 580 nm this emission intensity decreases more than 10 times, i.e. corresponds to 10% of the maximal emission intensity (FIG. 3a).

The maximal intensity of the substrate with immobilized TAMRA is shown in FIG. 3b. The maximal fluorescence intensity of this combination is observed at wavelength of 580 nm, while intensity of emission at 540 nm is 5 times less the peak value. Consequently, the impact of quantum dot emission on TAMRA emission main peak is around 2%. This low contribution excludes possibility of error accumulation and can be easily taken into account in calculations.

Method for determination of fluorescent analyte concentration through displacement of analyte analogue marked with fluorescent dye from the binding site can be used. For this method the binding sites of sensor molecule are preliminarily saturated with fluorescence reporter ligand, and in the presence of analyte this fluorescent ligand is displaced from the complex that decreases the observed FRET effect.

Figure 4:
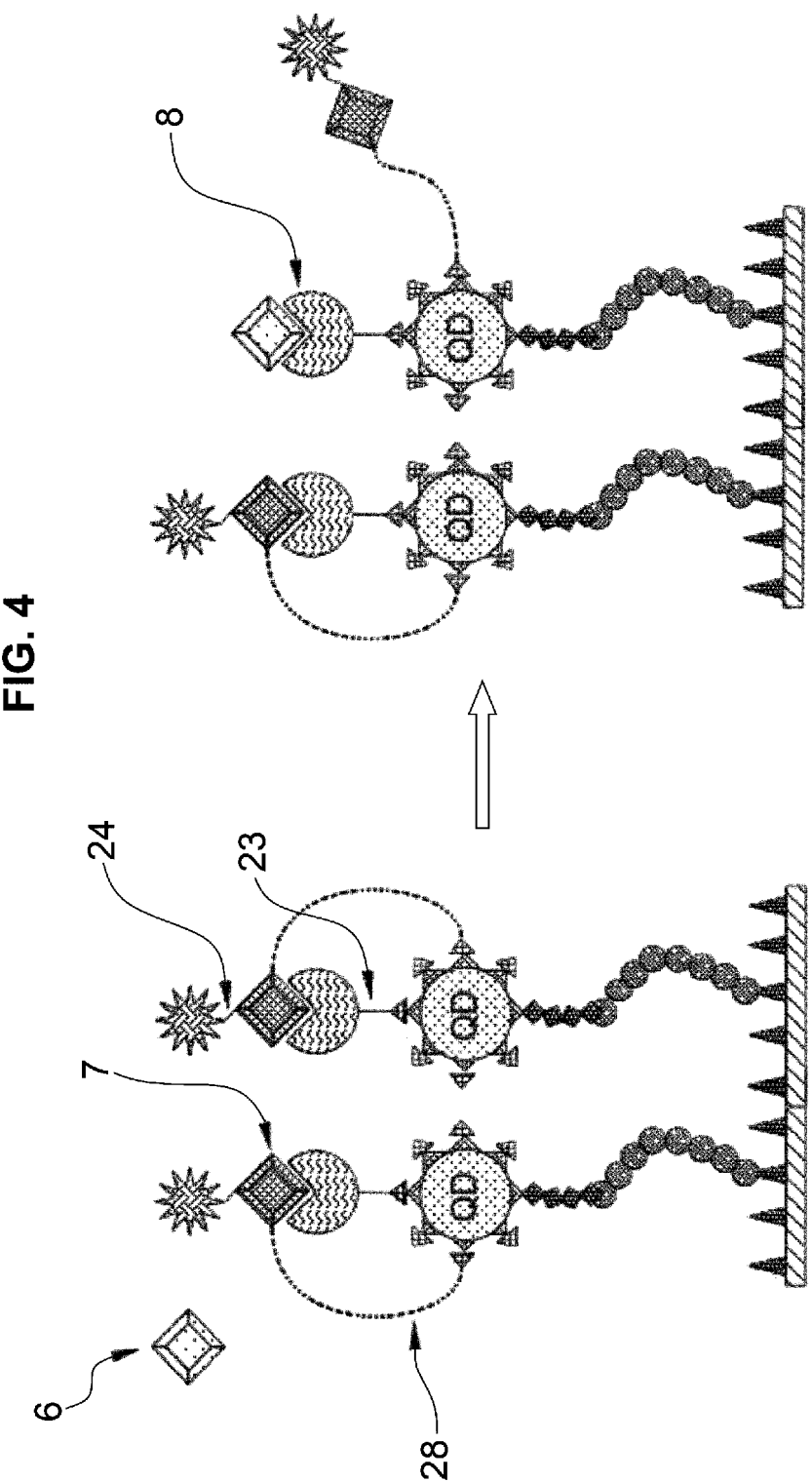
FIG. 4: Analyte interaction with assay substrate. Displacement method. 6—natural analyte; 7—dye-labeled analogue of analyte; 8—sensor molecule reversibly bound with the analyte analogue marked with fluorescent dye; 23—functional linker for covalent binding of sensor molecule (8) on QD; 24—linker for the second fluorescent marker; 28—linker connecting dye-labeled analogue of analyte with QD (2).

This displacement scheme is illustrated in FIG. 4, and dependence of the signal on analyte concentration can be characterized by a known mathematical function. The detection is based on the fact that transfer of the analyte molecule (6) from bulk solution into the binding site immobilized on the substrate stops the FRET effect that is monitored by the device. For this purpose the linker (28) binding the analyte analogue (7) with QD has a length exceeding the Förster radius. This linker prevents displaced analyte analogue to compete with the natural analyte for selective binding sites on another sensor molecule (8). It minimizes reverse effect of displacement, thus determining the kinetics and providing predictable result in the displacement method.

The length of linker (28) may be varied provided its minimum length is greater than the Förster radius for a selected FRET pair. The maximum length of linker (28) may vary according to a desired implementation. In some embodiments, the maximum length will be sufficiently short to reduce binding of the analyte analogue to a neighboring unlinked sensor molecule, such that an association rate of the analyte analogue to its corresponding linked sensor molecule is greater than an association rate of the analyte analogue to a neighboring sensor molecule that is not linked to the analyte analogue. In some embodiments, the maximum length of linker (28) is sufficiently short to prevent binding of the analyte analogue to a neighboring unlinked sensor molecule.

Figure 5:
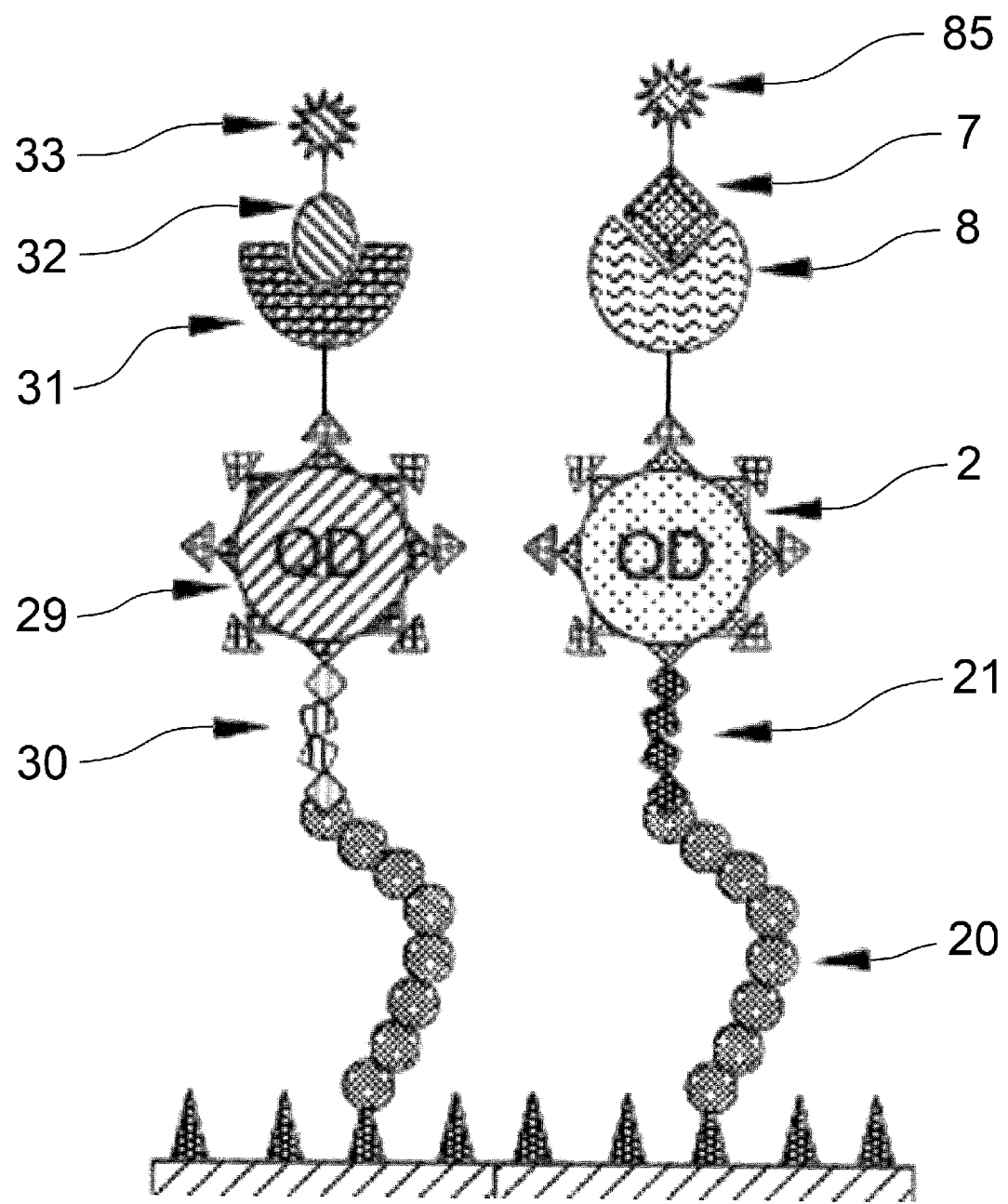
FIG. 5: Assay substrate with multiple senor systems immobilized on the surface with composite linkers: 2 and 29—different types of QD; 5 and 33—different types of fluorescent dye; 7 and 32—different types of analyte analogue; 8 and 31—different types of sensor molecule; 20—polymer linker; 21 and 30—different types of bi-polar linker.

The first option of sensor system embodiment for detection of multiple analytes is shown in FIG. 5. The use of composite linker consisting of polymer linker (20) and bi-polar linkers (21, 30) makes possible to immobilize quantum dots (2, 29) with different functional groups (22) on the same substrate surface. In turn, it allows binding different sensor molecules (8, 31) with reversibly bound different analyte analogues (7, 32) marked with different fluorescent markers (5, 33). As a result, multi-sensor system is constructed on the substrate surface for simultaneous detection of various analytes in a sample.

Figure 6:
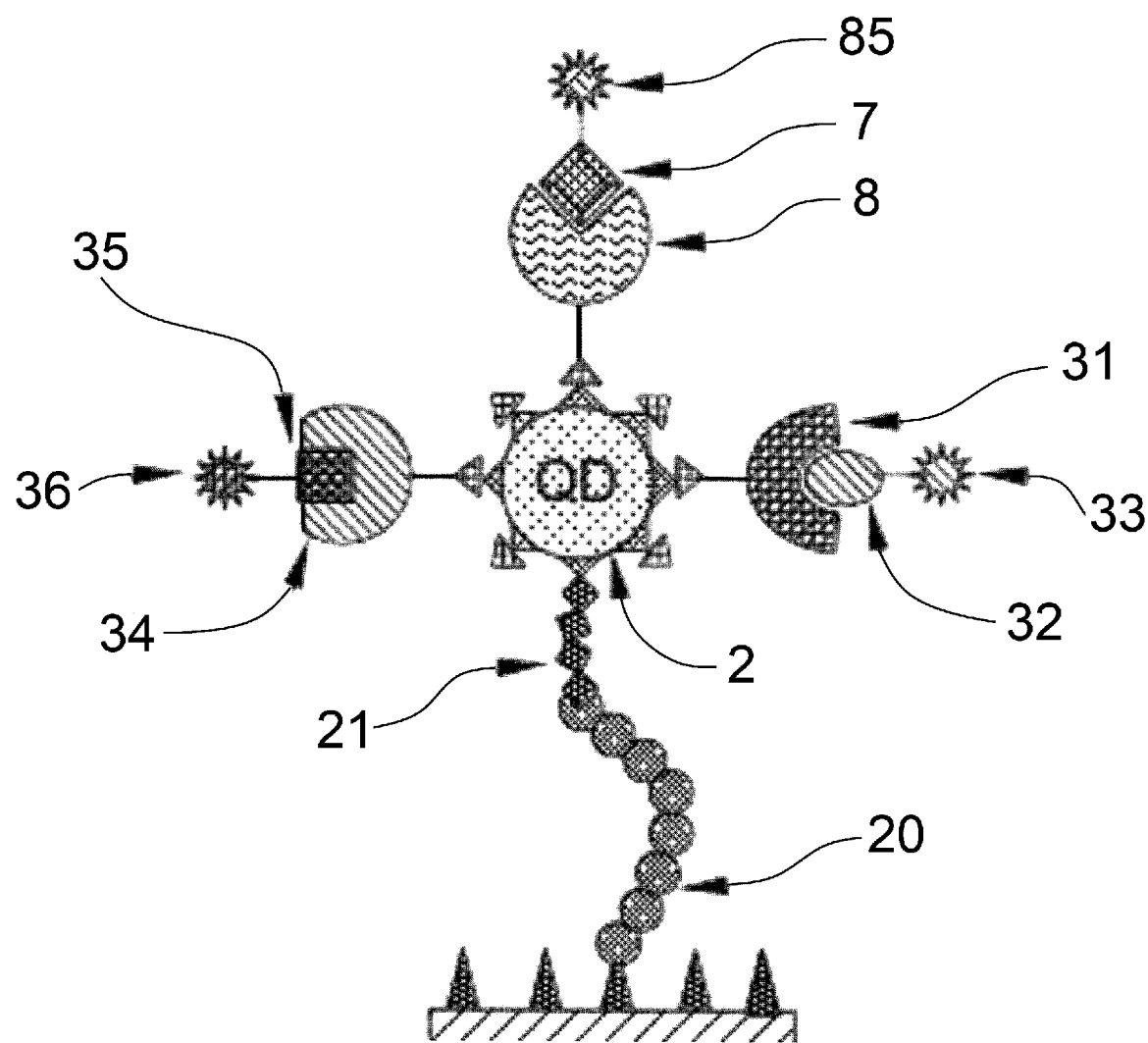
FIG. 6: Assay substrate with multiple senor systems bound with QD (2): 5, 33, 36—different types of fluorescent dye; 7, 32, 35—different types of analyte analogue; 8, 31, 34—different types of sensor molecule; 20—polymer linker; 21—bi-polar linker.

Another option of sensor system embodiment for detection of multiple analytes is shown in FIG. 6. It utilizes the features of chemical groups (22) planted on the surface of QD (2). In this embodiment the various sensor molecules (8, 31, 34) are bound with QD with following reversible binding with various analyte analogues (7, 32, 35). The immobilization of such sensor system on the substrate surface with linker (20, 21) makes possible to use various QD, thus integrating the features of the first option in the second option, thus providing extended multisensory system for simultaneous detection of a plurality of analytes.

The multispectral detection of the sensor system fluorescence according to both options allows distinguishing a variety of analytes with single assay substrate.

Figure 7:
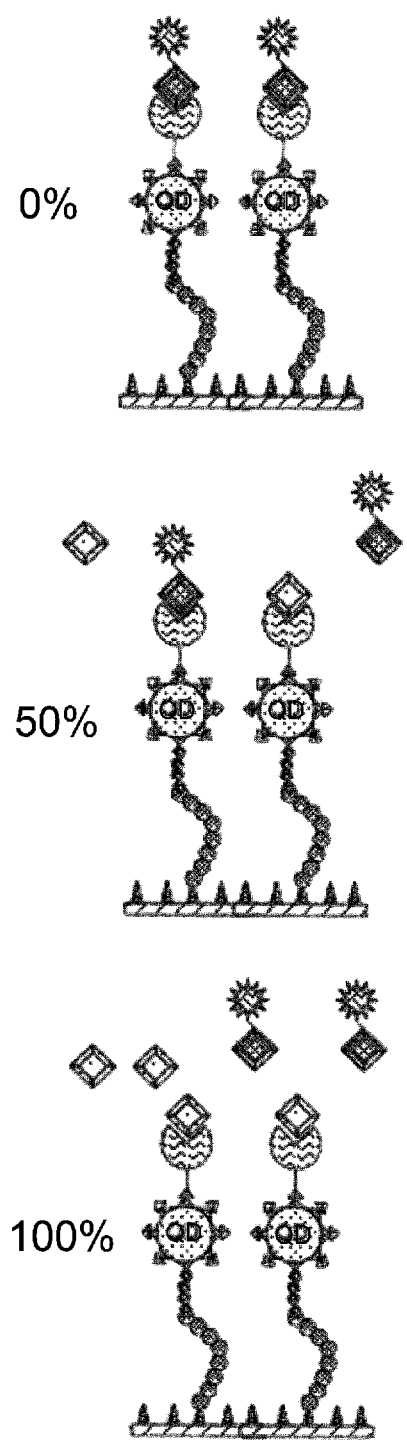
FIG. 7: Signal registration scheme of displacement method at different reaction stages that defined by analyte concentrations in samples: (a) very low or close to 0%; (b) concentration that enough to displace half dye-labeled analogues of analyte from bound sites; (c) saturation stage that defined by full displacement in binding sites.
Figure 7:
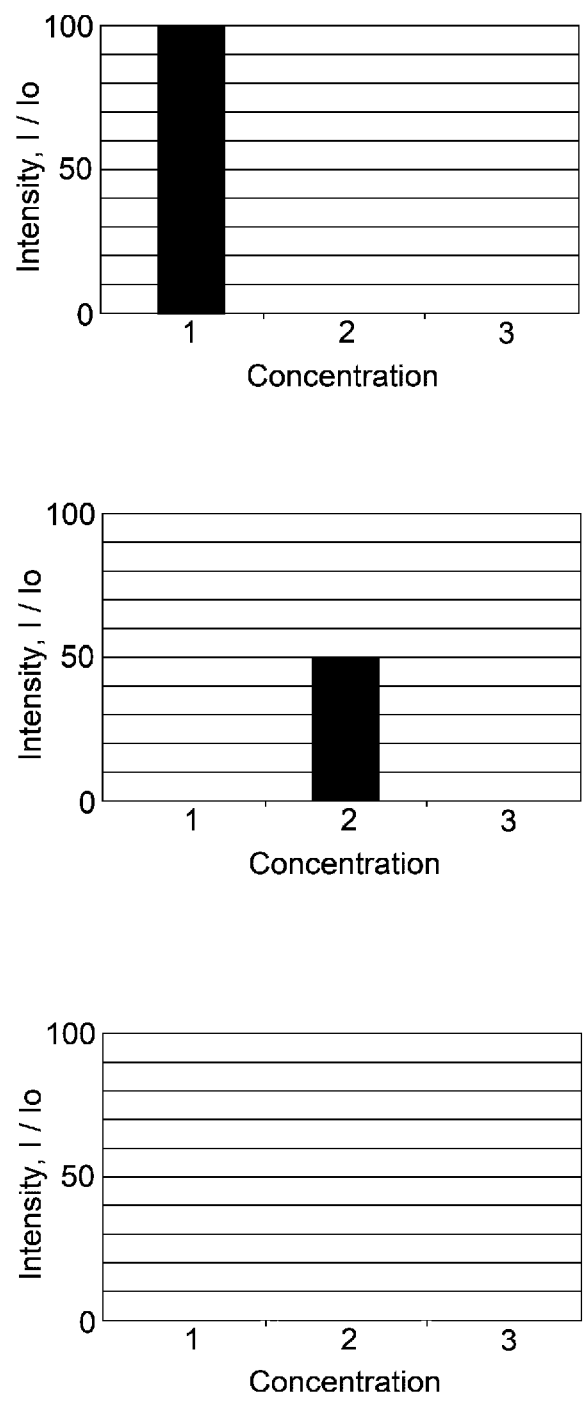

The binding process and signal generation are illustrated in FIG. 7. In the absence of analyte in medium liquid sample the detector monitors only the background signal (FIG. 7a). If half of the binding sites are occupied by the analyte, half of the maximal signal is detected (FIG. 7b), while the maximal signal corresponds to saturation of the binding sites (FIG. 7c), and further increase in analyte concentration cannot be detected. The absolute value of the maximal signal depends on number of binding sites. Plot of the signal for equilibrated system on analyte concentration has also some linear part, while at higher analyte concentrations a more complex function should be used for description of the plot.

Application of the displacement method significantly extends the list of analytes, which can be detected by using the assay substrate described, because analogs of analyte molecule can also displace the complex. However, this displacement takes place at different concentration interval and this can be used for differentiation of analyte analogue from true analyte.

The measuring system comprises substance-specific assay substrate and the device for inducing and detecting the specific fluorescence of the substrate. The multilayer composition of the substrate defines the specificity of the system for targeted analyte. The variation of the multilayer composition of the substrate allows detection of various analytes. Moreover, the setup of the single assay substrate with various multilayer compositions gives the possibility to detect different analytes in a sample simultaneously.

Figure 8:
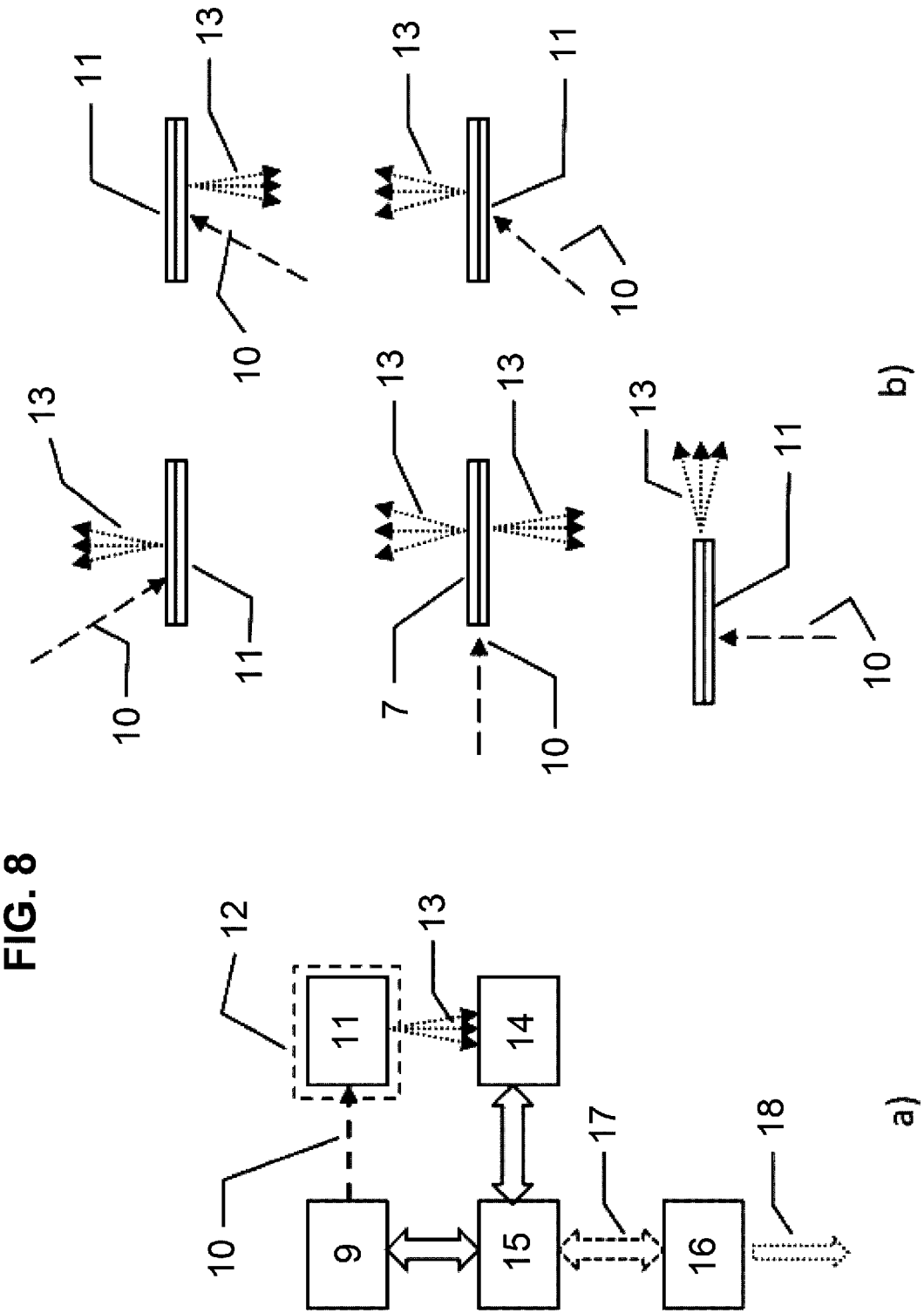
FIG. 8: a) Block-scheme of the device. b) Optical layouts of the assay substrate compartment: 9—light source, 10—light source emission, 11—assay substrate, 12—assay substrate compartment, 13—fluorescence flux, 14—optoelectronic detector, 15—controller; 16—control unit, 17—communication line.

The block scheme of the device for analyte detection with assay substrate is shown in FIG. 8a. The device consists of a light source (9) with characteristic light emission (10) at preselected wavelength to induce the assay substrate (11) fluorescence, the assay substrate compartment (12) to introduce and measure the assay substrate with liquid sample, the opto-electronic detector (14) to record the fluorescence (13) caused by FRET effect, the controller (15), to manage the measurements, control unit (16) to determine concentration of the analyte, and communication interface (17) to report the result.

The spectral characteristics of light source emission (10) correspond to the excitation spectrum of QD or other type first fluorescent marker for further energy transition to the second fluorescent marker on the assay substrate (11) due to FRET effect. Some embodiments of optical layouts of the substrate compartment (12) are depicted in FIG. 8b. The fluorescence emission (13) of a second fluorescent marker on the assay substrate (11) is detected by an opto-electronic detector (14). The detector can be of either single or multichannel layout. If the assay substrate contains several multilayer structures aimed for the detection of some analytes simultaneously, then multichannel detector can be used. In such embodiment every channel serves for detection of specific analyte. The controller (15) serves to operate the device and measure the decrease of the fluorescence intensity of the assay substrate over time according to schematics in FIG. 7. The communication line (17) provides wire- or wireless delivery of command to the device and measured data to the external control unit (16) to derive the concentration of an analyte from measured time curve of said fluorescence and for further visualization, storage and communication line (18) to report the data to the external recipient. The control unit (16) can be, but not limited to, computer, panel PC, tablet, smart phone etc., and the external recipient can be remote server, cloud database etc.

EXAMPLE

Figure 9:
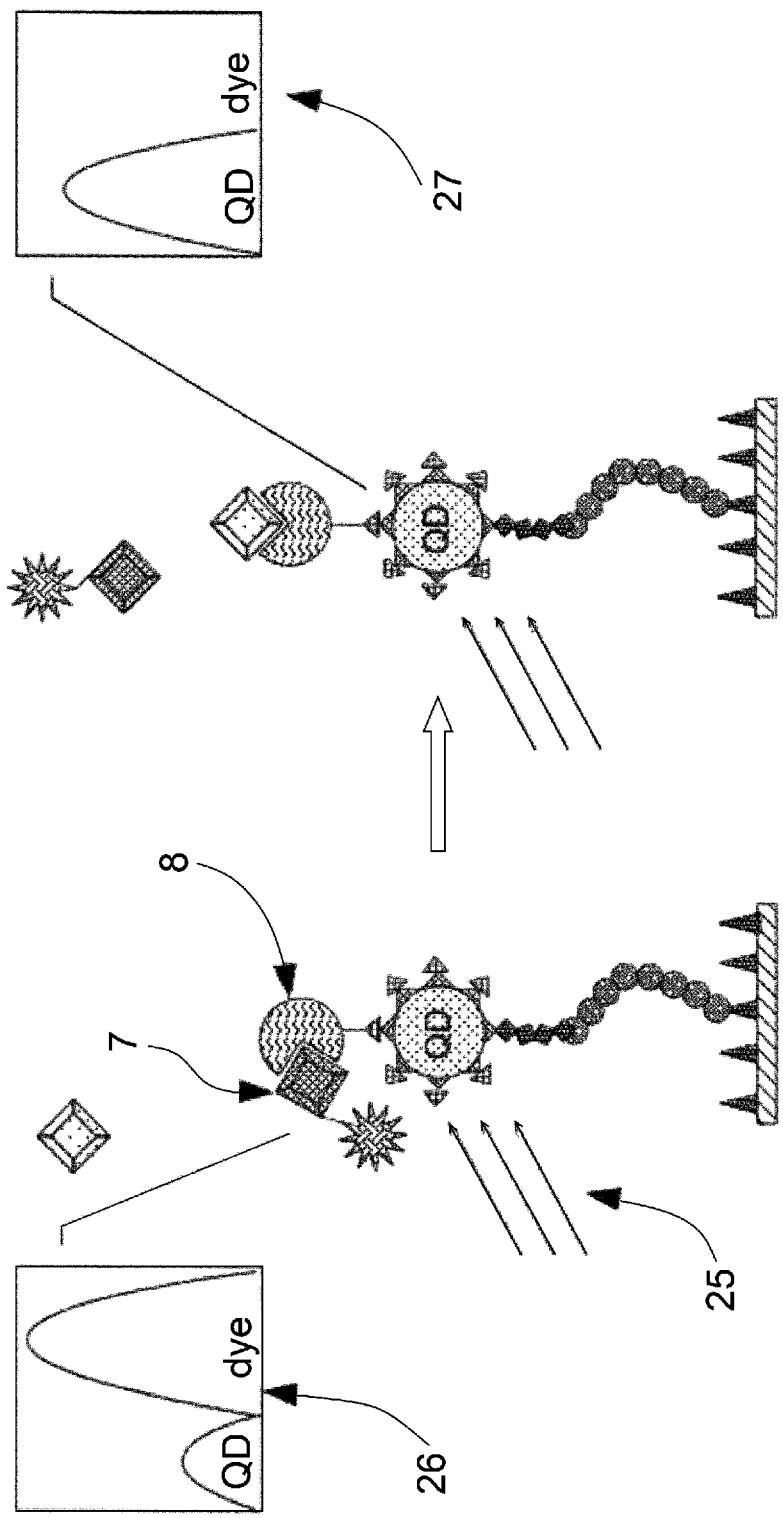
FIG. 9—Example: Illustration of principals of displacement method. 7—dye-labeled analogue of analyte; 8—sensor molecule reversibly bound with the analyte analogue marked with fluorescent dye; 25—excitation light; 26—initial emission spectrum of the substrate with FRET effect; 27—emission spectrum after displacement of the analyte analogue.

The following example illustrates applicability of the methods described herein without limiting the scope thereof, and concerns determination of concentration of an analyte which is a water-soluble bioactive molecule by using the displacement method as illustrated in FIG. 9.

Preparation of the Assay Substrate

The reaction mixture was prepared, consisting of the following components:

400 µL of 10 mM boronic acid saline buffer, containing 50 mM NaCl, pH 7.5

25 µL of QD suspension (1 mg/mL) in water,

90 µL (3 mM) 1,6-diaminohexane,

7 µL of 10 mM aptamer, which contains carboxyl groups

15 µL of mixture of EDC (20 mg/mL) and NHS (1 mg/mL).

This mixture was added to mica discs, preliminarily modified with (EtO)3Si(CH2)3NH2. The discs were incubated with the reaction mixture during 1 h, and then washed with water and dried in vacuum. For finishing synthesis of the substrate the modified mica discs were soaked in 10 mM phosphate buffer containing 150 mM NaCl, and specific TAMRA-labeled analyte analogue was added at concentration 4 µM. During 30 min incubation at room temperature TAMRA-labeled analyte analogue bound to the aptamer, and this process completed formation of the layered structure of the assay substrate, containing layers of covalently bound QD and aptamer reversibly bound to analyte analogue with TAMRA complex. As the QD and TAMRA were at close distance on the surface of this substrate, intensive FRET effect was observed in the emission spectral range 500-600 nm at the excitation wavelength of 320 nm. The emission spectra corresponded to TAMRA fluorescence with peak intensity at 580 nm.

Procedure of Analysis

The analyte solution containing components that imitate physiological conditions of a blood has been prepared. Solution pH was stabilized in range 7.0 to 7.5 by phosphate buffer with saline solution. To imitate protein components influence bovine serum albumine was used in concentration 6 g/dl in final solution. To test the assay the analyte solutions at 100 nM an 200 nM concentration were added to the mica discs and changes in fluorescence spectrum were detected. These changes reflect displacement of the TAMRA-labeled analyte analogue from its complex with the immobilized aptamer by analyte in the assay mixture. This displacement is accompanied with leaving of the TAMRA label from the assay substrate surface that stops the FRET effect between the fluorophore and QD.

The assay was performed in two modes. Firstly, the time-course of the decrease of the FRET effect was observed and the initial speed of this process was monitored. Secondly, the system was incubated until equilibrium state was achieved and then the FRET value was detected and used for characterization of the assay system.

Alteration of the FRET effect was illustrated by comparison of the QD emission intensity at 540 nm and TAMRA emission at 580 nm. Displacement of the TAMRA-labeled analyte analogue from the complex with immobilized aptamer initiated in the presence of analyte molecules in a sample was accompanied with disappearance of the FRET effect. As a result TAMRA fluorescence at 580 nm decreased, and QD fluorescence at 540 nm increased (26, 27). The summary of analysis of these spectral data is shown in Table 1.

Table 1. The ratios of fluorescence intensities of donor (QD, peak emission at 540 nm) to acceptor (TAMRA, peak emission at 580 nm) at corresponding wavelengths of 540 nm and 580 nm as a percentage of maximum levels.

TABLE 1

| Time, min | 100 nM | 200 nM |
| --- | --- | --- |
| 0 | 15.0% | 17.4% |
| 0.5 | 43.1% | 68.5% |
| 1.5 | 75.4% | 91.7% |
| 2 | 85.7% | 92.8% |
| 3 | 92.5% | 92.0% |
| 5 | 89.2% | 97.2% |

The displacement of the immobilized analyte analogue marked with TAMRA from the complex with the immobilized aptamer was also detected by measuring the emission level of TAMRA. Alterations of its fluorescence intensity in time of the experiments are shown in Table 2. The intensities normalized to the initial value demonstrated clear decrease in time. The output signal plateau was determined after 5 minutes at the 200 nM concentration of the analyte and after 15 minutes for 100 nM analyte solution.

Table 2. Intensity of TAMRA fluorescence emission at 580 nm. SPR

TABLE 2

| Time, min | 100 nM | 200 nM |
| --- | --- | --- |
| 0 | 100.0% | 100.0% |
| 0.5 | 95.7% | 72.3% |
| 1.5 | 92.7% | 52.8% |
| 2 | 91.5% | 42.9% |
| 3 | 73.9% | 31.4% |
| 5 | 60.6% | 13.2% |

Figure 10:
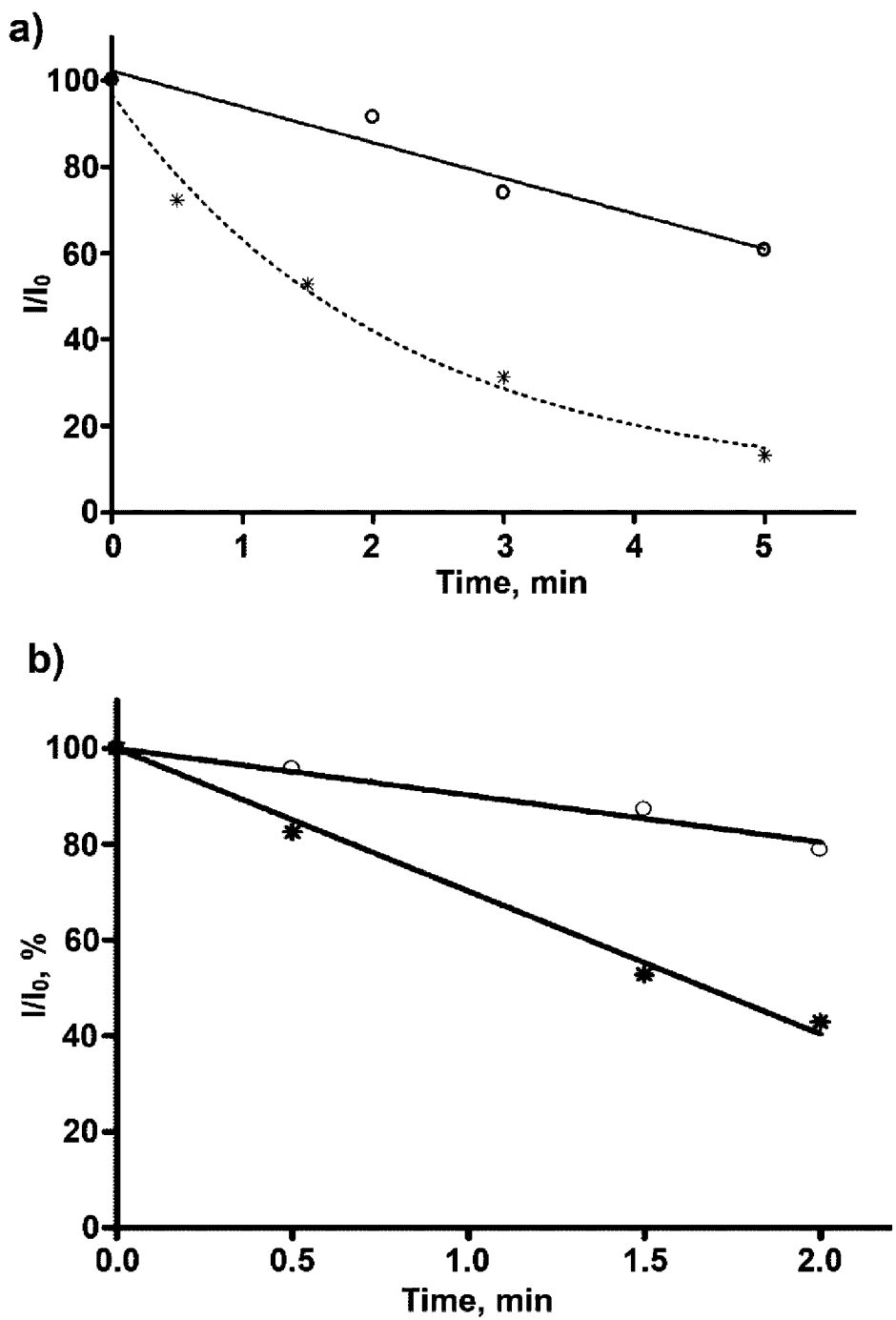
FIG. 10—Example: Dependence of emission intensity decay on time: (a) whole plot of reaction; (b) initial part of reaction.

The initial rate of complex dissociation, initiated by analyte in medium sample, was calculated from the slope of the initial linear part of the time-course of spectral changes. These plots are shown in FIG. 10. The slopes of the initial parts of the measured kinetic curves were different in the presence of 100 nM and 200 nM ligand solutions. Values of the initial rates are listed in Table 3. As results of the kinetic assay depend on time interval needed to reach the equilibrium state of the system that may be a significant source of uncertainly of the assay, results of the kinetic assay are more reliable. Moreover, these results can be obtained during several minutes that shortens the assay time. This aspect is very important if very potent analytes are assayed, as most of strong interactions between the substrate and analyte are slow.

Table 3. Initial reaction rate determination for different concentration of competitive analyte.

TABLE 3

| Analyte concentration, nM | Reaction rate, $\text{min}^{-1}$ |
|---|---|
| 100 | 9.8 ± 0.6 |
| 200 | 29.8 ± 1.0 |

Invention described above is not limited to the embodiments described above and depicted on illustrations, but said invention may have within the scope of the appended claims other embodiments

REFERENCES

Alsager O A, Kumar S, Willmott G R, McNatty K P, Hodgkiss J M. Small molecule detection in solution via the size contraction response of aptamer functionalized nanoparticles. Biosens Bioelectron. 2014 Jul. 15;57:262-8. doi: 10.1016/j.bios.2014.02.004.

Buchberger W W. Current approaches to trace analysis of pharmaceuticals and personal care products in the environment. J Chromatogr A. 2011 Jan. 28;1218(4):603-18. doi: 10.1016/j.chroma.2010.10.040.

Couto R A, Lima J L, Quinaz M B. Recent developments, characteristics and potential applications of screen-printed electrodes in pharmaceutical and biological analysis. Talanta. 2016 Jan. 1;146:801-14. doi: 10.1016/j.talanta.2015.06.011.

Farré M, Petrovic M, Barceló D. Recently developed GC/MS and LC/MS methods for determining NSAIDs in water samples. Anal Bioanal Chem. 2007 February;387(4):1203-14.

Kodoyianni V. Label-free analysis of biomolecular interactions using SPR imaging. Biotechniques. 2011 January;50(1):32-40. doi: 10.2144/000113569.

Lakowicz J. R. Principles of Fluorescent Spectroscopy, 3rd Edn. New York, N.Y.: Springer, 2006. doi: 10.1007/978-0-387-46312-4.

Lara F J, Airado-Rodriguez D, Moreno-González D, Huertas-Pérez J F, García-Campaña A M. Applications of capillary electrophoresis with chemiluminescence detection in clinical, environmental and food analysis. A review. Anal Chim Acta. 2016 Mar.24;913:22-40. doi: 10.1016/j.aca.2016.01.046.

Long F, Zhu A, Shi H. Recent advances in optical biosensors for environmental monitoring and early warning. Sensors (Basel). 2013 Oct. 15;13(10):13928-48. doi: 10.3390/s131013928.

Nguyen B, Tanious F A, Wilson W D. Biosensor-surface plasmon resonance: quantitative analysis of small molecule-nucleic acid interactions. Methods. 2007 June;42(2):150-61.

Petrovic M, Farré M, de Alda M L, Perez S, Postigo C, Köck M, Radjenovic J, Gros M, Barcelo D. Recent trends in the liquid chromatography-mass spectrometry analysis of organic contaminants in environmental samples.

J Chromatogr A. 2010 Jun. 18;1217(25):4004-17. doi: 10.1016/j.chroma.2010.02.059.

Staples C A, Naylor C G, Williams J B, Gledhill W E. Ultimate biodegradation of alkylphenol ethoxylate surfactants and their biodegradation intermediates. Environ Toxicol Chem. 2001 November;20(11):2450-5.

Xu Y, Yang X, Wang E. Review: Aptamers in microfluidic chips. Anal Chim Acta. 2010 Dec. 17;683(1):12-20. doi: 10.1016/j.aca.2010.10.007.

Zhou D, Ying L, Hong X, Hall E A, Abell C, Klenerman D. A compact functional quantum Dot-DNA conjugate: preparation, hybridization, and specific label-free DNA detection. Langmuir. 2008 Mar. 4;24(5):1659-64. doi: 10.1021/la703583u.

The invention claimed is:

1. A device for detection of an organic analyte in a liquid sample, the device comprising:
   an assay substrate configured with an assay substrate surface comprising a first component and a second component;
   the first component comprising a sensor molecule labeled with a first fluorescent marker immobilized to the assay substrate surface with a first linker, the first linker being a bi-polar linker comprising a first binding group for specific binding of the first fluorescent marker and a second binding group for specific binding of the assay substrate surface, the sensor molecule having a specific binding site for the organic analyte, the sensor molecule labeled with the first fluorescent marker in a position that has no effect on the organic analyte binding the specific binding site;
   the second component comprising a chemical analogue of the organic analyte, the chemical analogue labeled with a second fluorescent marker, the chemical analogue linked to the first fluorescence marker with a second linker having a length exceeding Föster radius, and the chemical analogue reversibly binding the specific binding site of the sensor molecule of the first component;
   the assay substrate defining an assay substrate compartment for applying the liquid sample to the assay substrate surface;
   a light source configured to emit a specific spectrum to excite fluorescence of the first fluorescent marker;
   an opto-electronic detector configured to detect fluorescence of the second fluorescent marker and generate a signal corresponding to fluorescence intensity; and
   a controller configured to record the signal from the opto-electronic detector and determine presence of the organic analyte based on a decrease of the detected fluorescence;
   wherein the first fluorescent marker is a quantum dot (QD) having a first fluorescence emission spectrum that excites fluorescence of the second fluorescent marker and the second fluorescent marker is a fluorescent dye having a second fluorescence emission spectrum distinguished from the first fluorescence spectrum of the first fluorescent marker.

2. The device of claim 1, wherein the controller is configured to record the signal generated by the opto-electronic detector in time to record a time curve of the detected fluorescence to determine the concentration of the organic analyte.

3. The device of claim 2, wherein the controller is configured to derive concentration of an analyte by relative decrease of recorded fluorescence in time from its initial value.

4. The device of claim 1, wherein the second linker is sized to prevent binding of the chemical analogue with a specific binding site of a neighboring first component unlinked to the chemical analogue.

5. The device of claim 4, wherein the sensor molecule is labeled with the first fluorescent marker by a third linker linking the sensor molecule to the first fluorescent marker, a length of the third linker being shorter than the Föster radius and being shorter than the length of the second linker.

6. The device of claim 1, wherein the assay substrate is configured to bind a plurality of types of organic analytes, a plurality of types of sensor molecules respectively labeled with a plurality of types of first fluorescence markers immobilized on the same assay substrate surface, and the controller configured to process a detected fluorescence having multi-spectral characteristics.

7. The device of claim 1, wherein a thickness of interaction surface layer of the liquid sample applied onto the assay substrate is limited according to the Förster radius.

8. A method for detection of an organic analyte in a liquid sample, the method comprising:
(a) obtaining the device according to claim 1, the first and the second components of the assay substrate surface interacting to position the first fluorescent marker close to the second fluorescent marker at a distance shorter than the Förster radius to enable a FRET effect between the first and second fluorescent markers;
(b) applying the liquid sample to the assay substrate;
(c) illuminating the assay substrate with a light that excites fluorescence of the first fluorescent marker;
(d) detecting fluorescence of the second fluorescent marker; and
(e) detecting the organic analyte by determining a decrease in fluorescence of the second fluorescent marker, due to the organic analyte displacing the chemical analogue from the specific binding site and subsiding the FRET effect.

9. The method of claim 8, further comprising quantifying a concentration of the organic analyte in the liquid sample by recording a time curve of the decrease in the detected fluorescence of the second fluorescent marker.

10. The method of claim 8, further comprising quantifying an amount of the organic analyte in the liquid sample by measuring the decrease in the detected fluorescence of the second fluorescent marker, the degree of the measured decrease corresponding to the amount of the organic analyte in the liquid sample.

11. The method of claim 8, wherein the second linker is sized to prevent binding of the chemical analogue with a specific binding site of a neighboring first component unlinked to the chemical analogue.

12. The method of claim 11, wherein the sensor molecule is labeled with the first fluorescent marker by a third linker linking the sensor molecule to the first fluorescent marker, a length of the third linker being shorter than the Föster radius and being shorter than the length of the second linker.

13. The method of claim 8, wherein the assay substrate is configured to bind a plurality of types of organic analytes, a plurality of types of sensor molecules respectively labeled with a plurality of types of first fluorescence markers immobilized on the same assay substrate surface, and the detected fluorescence having multi-spectral characteristics.

14. The method of claim 8, wherein the detecting of the organic analyte occurs in a thin layer of the liquid sample, the thickness of an interaction surface layer of the liquid sample on the assay substrate being limited according to the Förster radius.

15. The method of claim 8, wherein the liquid sample is applied without any preparation and/or pretreatment.

16. The method of claim 8, wherein the liquid sample is applied at a volume of no more than a microliter.

* * * * *